(12) United States Patent
Huang et al.

(10) Patent No.: US 12,213,844 B2
(45) Date of Patent: Feb. 4, 2025

(54) OPERATION IMAGE POSITIONING METHOD AND SYSTEM THEREOF

(71) Applicant: METAL INDUSTRIES RESEARCH & DEVELOPMENT CENTRE, Kaohsiung (TW)

(72) Inventors: Bing-Feng Huang, Kaohsiung (TW); Jin-Yuan Syue, Tainan (TW); Bo Siang Tsai, Tainan (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 214 days.

(21) Appl. No.: 18/146,390

(22) Filed: Dec. 26, 2022

(65) Prior Publication Data

US 2024/0207012 A1 Jun. 27, 2024

(51) Int. Cl.
*G06T 5/50* (2006.01)
*A61B 6/00* (2024.01)
*A61B 6/04* (2006.01)
*A61B 90/00* (2016.01)

(52) U.S. Cl.
CPC .......... *A61B 90/361* (2016.02); *A61B 6/4405* (2013.01); *A61B 6/4441* (2013.01); *G06T 5/50* (2013.01); *G06T 2207/10116* (2013.01); *G06T 2207/20221* (2013.01)

(58) Field of Classification Search
CPC ... A61B 6/4405; A61B 6/4441; A61B 90/361; G06T 5/50; G06T 2207/10116; G06T 2207/20221
See application file for complete search history.

(56) References Cited

U.S. PATENT DOCUMENTS

| 10,719,953 | B1 | 7/2020 | Ye et al. |
| 10,729,502 | B1 * | 8/2020 | Wolf ...................... A61B 5/746 |
| 11,553,969 | B1 * | 1/2023 | Lang ..................... G06T 7/0012 |

(Continued)

FOREIGN PATENT DOCUMENTS

| TW | I410893 B | 10/2013 |
| TW | I669683 B | 8/2019 |

(Continued)

*Primary Examiner* — Mark R Gaworecki
(74) *Attorney, Agent, or Firm* — CKC & Partners Co., LLC

(57) ABSTRACT

An operation image positioning method is disclosed. A point-cloud camera captures a point-cloud image of first and second positioning marks respectively fixed on a treated portion and an X-ray imaging machine. The first and second positioning marks within the point-cloud image are recognized to compute a first conversion module between the point-cloud camera and the treated portion and a second conversion module between the point-cloud camera and the X-ray imaging machine, thereby computing a third conversion module between the treated portion and the X-ray imaging machine. An image positioning camera captures a positioning image of the first positioning mark. The first positioning mark within the positioning image is recognized to compute a fourth conversion module between the image positioning camera and the treated portion. A fifth conversion module between the image positioning camera and the X-ray imaging machine is computed according to the third and fourth conversion modules.

15 Claims, 4 Drawing Sheets

(56) References Cited

U.S. PATENT DOCUMENTS

| | | | |
|---|---|---|---|
| 2019/0000564 A1 | 1/2019 | Navab et al. | |
| 2019/0380792 A1* | 12/2019 | Poltaretskyi | G09B 23/28 |
| 2023/0196595 A1* | 6/2023 | Grupp, Jr. | G06T 7/70 |
| | | | 382/294 |
| 2023/0210604 A1* | 7/2023 | Berman | A61B 90/37 |
| | | | 378/177 |

FOREIGN PATENT DOCUMENTS

| | | | | |
|---|---|---|---|---|
| WO | WO-2021016429 A1 * | 1/2021 | | A61B 34/10 |
| WO | WO-2021115855 A1 * | 6/2021 | | A61B 6/027 |

* cited by examiner

OPERATION IMAGE POSITIONING METHOD AND SYSTEM THEREOF

BACKGROUND

Field of Invention

The present invention relates to an operation image positioning method and an operation image positioning system. More particularly, the present invention relates to an operation image positioning method and an operation image positioning system using a point-cloud camera and an image positioning camera.

Description of Related Art

At present, during orthopedic surgery or spinal surgery, medical personnel often need to insert some implants into the human body. In order to accurately place implants in the correct position, in recent years, computer-assisted positioning surgical image navigation technology has been gradually developed to improve the positioning accuracy during surgery.

One of the core technologies of surgical image navigation technology is to align the X-ray images obtained during surgery with the stereographic images captured before surgery so as to create virtual instrument projected onto the stereographic images so that doctors can refer to and confirm the relative relationship between the instrument and the lesion. Therefore, whether the spatial relationship between the X-ray image capturing position and the positioning point on the capturing target is accurate will directly affect the accuracy of surgical image navigation. If the error generated here is too large, the cumulative error will continue to be generated in the subsequent navigation. Therefore, how to reduce errors to improve the accuracy of surgical image navigation is a topic of concern to those skilled in the art.

SUMMARY

The present invention provides an operation image positioning method executed by a computer system. The operation image positioning method includes: capturing a point-cloud image by a point-cloud camera, in which the point-cloud image contains a first positioning mark and a second positioning mark, in which the first positioning mark is fixed on a treated portion and the second positioning mark is fixed on an X-ray imaging machine; recognizing the first positioning mark within the point-cloud image by the computer system so as to compute a first conversion module between the point-cloud camera and the treated portion; recognizing the second positioning mark within the point-cloud image by the computer system so as to compute a second conversion module between the point-cloud camera and the X-ray imaging machine; computing a third conversion module between the treated portion and the X-ray imaging machine, by the computer system, according to the first conversion module and the second conversion module; capturing a positioning image by an image positioning camera, in which the positioning image contains the first positioning mark; recognizing the first positioning mark within the positioning image by the computer system so as to compute a fourth conversion module between the image positioning camera and the treated portion; and computing a fifth conversion module between the image positioning camera and the X-ray imaging machine, by the computer system, according to the third conversion module and the fourth conversion module.

In accordance with one or more embodiments of the invention, the operation image positioning method further includes: capturing an X-ray image of the treated portion by the X-ray imaging machine; and combining the X-ray image and the positioning image according to the fifth conversion module, by the computer system, so as to provide a navigation interface.

In accordance with one or more embodiments of the invention, the X-ray imaging machine is a C-arm X-ray equipment having a transmitted part and a received part, and the second positioning mark is fixed on the received part.

In accordance with one or more embodiments of the invention, each of the first positioning mark and the second positioning mark has a structural feature recognized by the point-cloud camera, and the structural feature of the first positioning mark is different from the structural feature of the second positioning mark.

In accordance with one or more embodiments of the invention, each of the first positioning mark and the second positioning mark has a pattern recognized by the image positioning camera, wherein the pattern of the first positioning mark is different from the pattern of the second positioning mark.

In accordance with one or more embodiments of the invention, the first conversion module is a first matrix $T_A^C$, and the second conversion module is a second matrix $T_B^C$, and the third conversion module is a third matrix $T_B^A$, and $T_B^C = T_A^C \times T_B^A$.

In accordance with one or more embodiments of the invention, the fourth conversion module is a fourth matrix $T_A^P$, and the fifth conversion module is a fifth matrix $T_B^P$, and $T_B^P = T_A^P \times T_B^A$.

The present invention further provides an operation image positioning system. The operation image positioning system includes a first positioning mark fixed on a treated portion, a second positioning mark fixed on an X-ray imaging machine, a point-cloud camera operable to capture a point-cloud image, an image positioning camera arranged operable to capture a positioning image, and a computer system. The point-cloud image contains the first positioning mark and the second positioning mark. The positioning image contains the first positioning mark. The computer system is communicatively connected to the point-cloud camera and the image positioning camera so as to receive the point-cloud image and the positioning image. The computer system performs steps of: recognizing the first positioning mark within the point-cloud image so as to compute a first conversion module between the point-cloud camera and the treated portion; recognizing the second positioning mark within the point-cloud image so as to compute a second conversion module between the point-cloud camera and the X-ray imaging machine; computing a third conversion module between the treated portion and the X-ray imaging machine according to the first conversion module and the second conversion module; recognizing the first positioning mark within the positioning image so as to compute a fourth conversion module between the image positioning camera and the treated portion; and computing a fifth conversion module between the image positioning camera and the X-ray imaging machine according to the third conversion module and the fourth conversion module.

In accordance with one or more embodiments of the invention, the X-ray imaging machine is operable to capture an X-ray image of the treated portion. The computer system is communicatively connected to the X-ray imaging machine. The computer system further performs steps of:

combining the X-ray image and the positioning image according to the fifth conversion module so as to provide a navigation interface.

In accordance with one or more embodiments of the invention, the X-ray imaging machine is a C-arm X-ray equipment having a transmitted part and a received part, and the second positioning mark is fixed on the received part.

In accordance with one or more embodiments of the invention, each of the first positioning mark and the second positioning mark has a structural feature recognized by the point-cloud camera, and the structural feature of the first positioning mark is different from the structural feature of the second positioning mark.

In accordance with one or more embodiments of the invention, each of the first positioning mark and the second positioning mark has a pattern recognized by the image positioning camera, wherein the pattern of the first positioning mark is different from the pattern of the second positioning mark.

In accordance with one or more embodiments of the invention, the first conversion module is a first matrix $T_A^C$, and the second conversion module is a second matrix $T_B^C$, and the third conversion module is a third matrix $T_B^A$, and $T_B^C = T_A^C \times T_B^A$.

In accordance with one or more embodiments of the invention, the fourth conversion module is a fourth matrix $T_A^P$, and the fifth conversion module is a fifth matrix $T_B^P$, and $T_B^P = T_A^P \times T_B^A$.

In accordance with one or more embodiments of the invention, the point-cloud camera is a depth camera or a LiDAR scanner, and the image positioning camera is a visible light camera.

In order to let above mention of the present invention and other objects, features, advantages, and embodiments of the present invention to be more easily understood, the description of the accompanying drawing as follows.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Specific embodiments of the present invention are further described in detail below with reference to the accompanying drawings, however, the embodiments described are not intended to limit the present invention and it is not intended for the description of operation to limit the order of implementation. The using of "first", "second", "third", etc. in the specification should be understood for identify units or data described by the same terminology, but are not referred to particular order or sequence.

Figure 1:
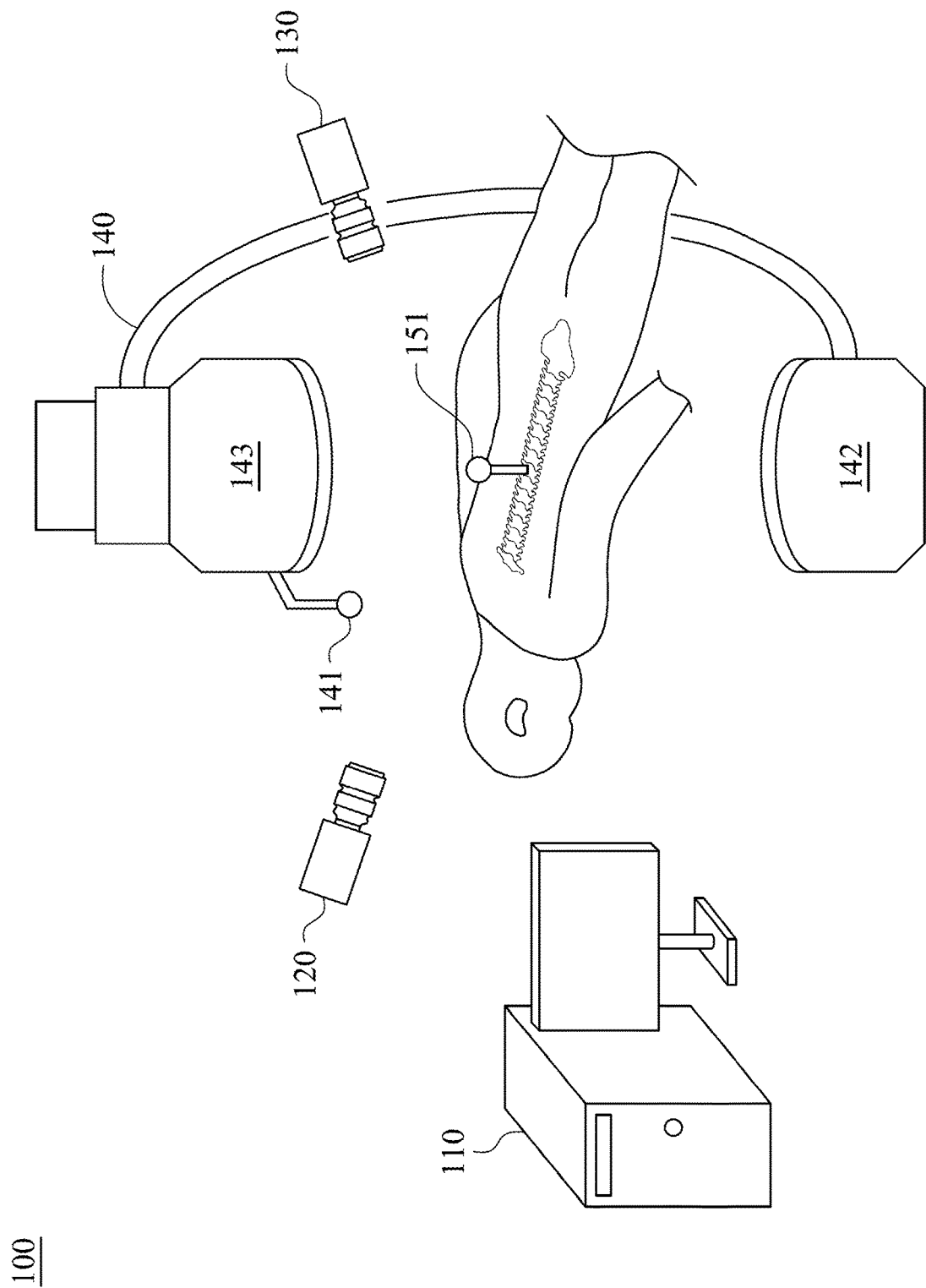
FIG. 1 illustrates a block diagram of an operation image positioning system according to some embodiments of the present invention.

FIG. 1 illustrates a block diagram of an operation image positioning system 100 according to some embodiments of the present invention. The operation image positioning system 100 includes a computer system 110, an image positioning camera 120, a point-cloud camera 130, an X-ray imaging machine 140, a positioning mark 141, and a positioning mark 151.

The image positioning camera 120 is used for photography so as to generate a positioning image. The image positioning camera 120 is, for example, a visible light camera. The positioning image is, for example, a visible light image. The image positioning camera 120 includes a charge-coupled device (CCD) sensor, a complementary metal-oxide semiconductor (CMOS) sensor or other suitable photosensitive elements, but the present invention is not limited thereto. The point-cloud camera 130 is used for photography so as to generate a point-cloud image. The point-cloud camera 130 is a 3D scanner for point cloud scanning, such as a depth camera, a LiDAR (Light Detection and Ranging) scanner or other computer vision devices.

Compared with the image positioning camera 120, the point-cloud camera 130 is used to provide more accurate image information to improve the error of capturing position. For example, if the image positioning camera 120 is used to record the position of the positioning mark, the root mean square error (RMSE) of the spatial positioning is about 0.5 millimeters (mm). Therefore, when calculating the spatial relationship, the maximum error between the positioning mark and the X-ray imaging machine 140 may reach 1 mm. In other words, the image positioning camera can obtain the posture of the positioning mark in real time, but the error is large. Relatively speaking, if we record the position of the positioning mark through the point cloud scanning of the point-cloud camera 130, the error of the spatial relationship between the positioning mark and the X-ray imaging machine 140 can ne reduce to the error value of the point cloud scanning itself (i.e., 0.1 mm). Therefore, although the point-cloud camera needs a long calculation time to obtain the posture of the positioning mark, the error is small. When the X-ray imaging machine performs photography, compared with the surgical action, the X-ray imaging machine and the treated portion (the surgical site) are relatively static. Therefore, there is no need for real-time positioning. And thus, the present invention can cooperate with point cloud scanning to reduce error.

The X-ray imaging machine 140 is used for photography so as to generate an X-ray image. The X-ray imaging machine 140 is a C-arm X-ray equipment. The C-arm X-ray equipment has a transmitted part 142 and a received part 143. The transmitted part 142 is used for emitting X-rays to the received part 143 to capture the X-ray image. The transmitted part 142 and the received part 143 can be rotated through a C-arm between the transmitted part 142 and the received part 143, so that the C-arm X-ray equipment can provide X-ray images from different angles.

The computer system 110 is communicatively connected to the image positioning camera 120, the point-cloud camera 130 and the X-ray imaging machine 140. The said connection can be achieved through any wired or wireless communication means. The computer system 110 is used for receiving the positioning image, the point-cloud image and the X-ray image, and performing image processing on them. The computer system 110 may be a smart phone, a tablet computer, a personal computer, a notebook computer, a server, an industrial computer, or various electronic devices with computing capabilities, etc., but the present invention is not limited thereto.

Specifically, the computer system 110 is used to provide a navigation interface (a surgical navigation interface) according to the images captured by the image positioning camera 120, the point-cloud camera 130 and the X-ray imaging machine 140, thereby displaying the location of the treated portion (the surgical site). In some embodiments, the navigation interface can be displayed on the screen of the computer system 110, but in some other embodiments, the navigation interface can also be displayed on the head-mounted device, the tablet computer, or the transparent display, but the present invention is not limited thereto. Herein, any virtual reality (VR) technology, augmented reality (AR) technology, alternative reality technology or mixed reality technology can be used to form the navigation interface, but the present invention is not limited thereto.

The positioning mark 141 is fixed on the received part 143 of the X-ray imaging machine 140. When the transmitted part 142 and received part 143 of the X-ray imaging machine 140 are rotated through the C-arm, the position of the positioning mark 141 will also change accordingly, so that the positioning mark 141 can be used to track the position of the received part 143. The positioning mark 151 is fixed on the treated portion. For example, if an operation is to be performed on the patient's spine, the positioning mark 151 is fixed on the patient's spine bone. When the patient's posture changes, the position of the positioning mark 151 will also change accordingly, so that the positioning mark 151 can be used to track the position of the spine bone. In some other embodiments, the positioning mark 151 may also be fixed on other body parts of the patient, but the present invention is not limited thereto.

Each of the positioning mark 141 and the positioning mark 151 has a specific pattern that can be recognized by the image positioning camera 120, and the specific pattern on the positioning mark 141 is different from the specific pattern on the positioning mark 151. Specifically, after receiving the positioning image from the image positioning camera 120, the computer system 110 can recognize the positioning mark 141 and the positioning mark 151 within the positioning image through image processing method or computer vision method. For example, the specific pattern on the positioning mark 141 and the specific pattern on the positioning mark 151 are known, so that the computer system 110 can recognize the positioning mark 141 and the positioning mark 151 within the positioning image according to the preset patterns respectively corresponding to the positioning mark 141 and the positioning mark 151, and respectively record their positions (the positions of the positioning mark 141 and the positioning mark 151) relative to the image positioning camera 120.

Each of the positioning mark 141 and the positioning mark 151 has a specific structural feature (such as a bump, but the present invention is not limited here) that can be recognized by the point-cloud camera 130, and the specific structural feature of the positioning mark 141 is different from the specific structural feature of the positioning mark 151. Specifically, after receiving the point-cloud image from the point-cloud camera 130, the computer system 110 can recognize the positioning mark 141 and the positioning mark 151 within the point-cloud image through image processing method or computer vision method. For example, the specific structural features on the positioning mark 141 and the specific structural features on the positioning mark 151 are known, so that the computer system 110 can recognize the positioning mark 141 and the positioning mark 151 within the point-cloud image according to the specific structural features respectively corresponding to the positioning mark 141 and the positioning mark 151, and respectively record their positions (the positions of the positioning mark 141 and the positioning mark 151) relative to the point-cloud cameras 130.

Figure 2:
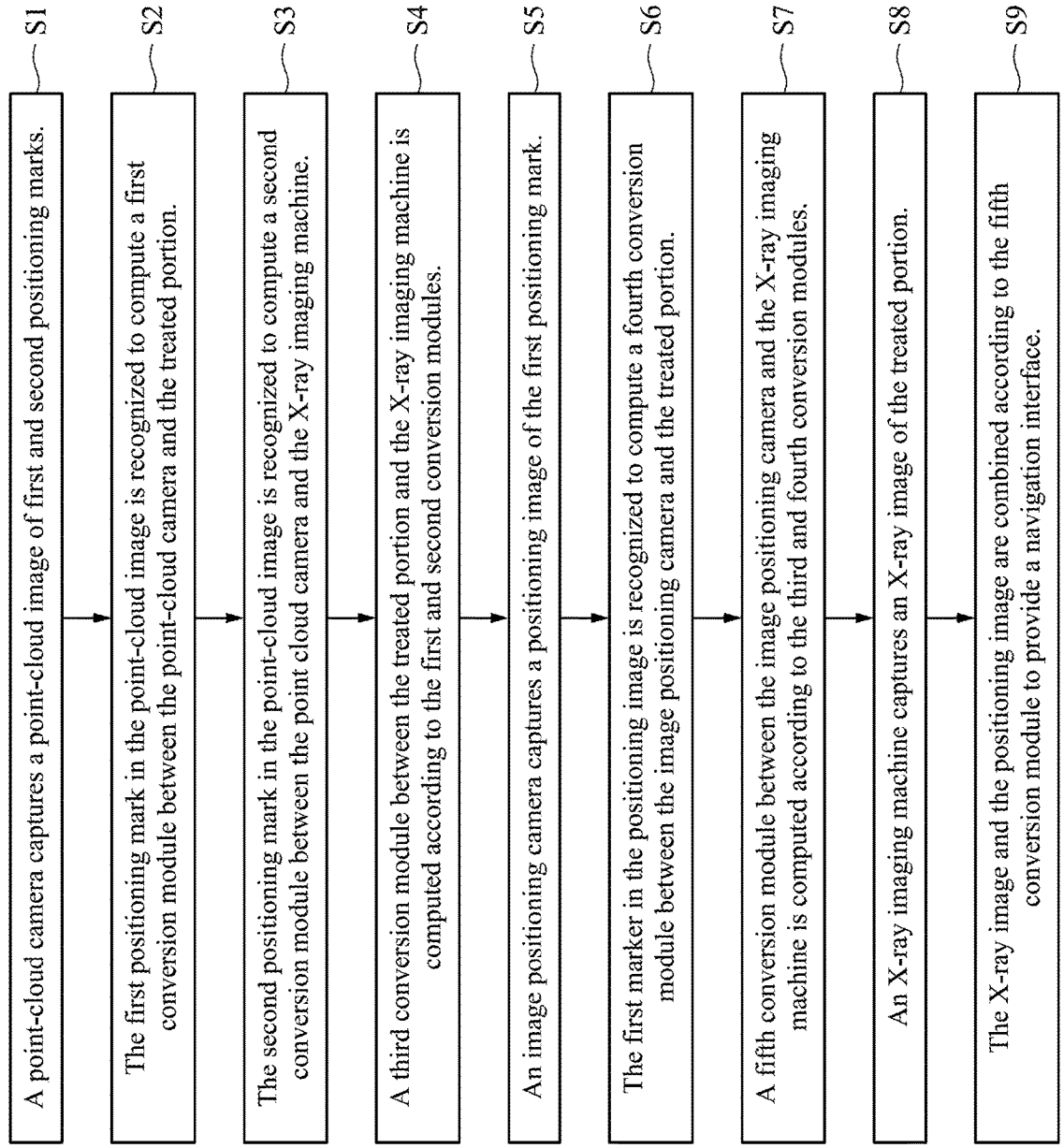
FIG. 2 illustrates a flowchart of an operation image positioning method according to some embodiments of the present invention.

FIG. 2 illustrates a flowchart of an operation image positioning method 1000 according to some embodiments of the present invention. The operation image positioning method 1000 includes steps S1-S9.

Figure 3:
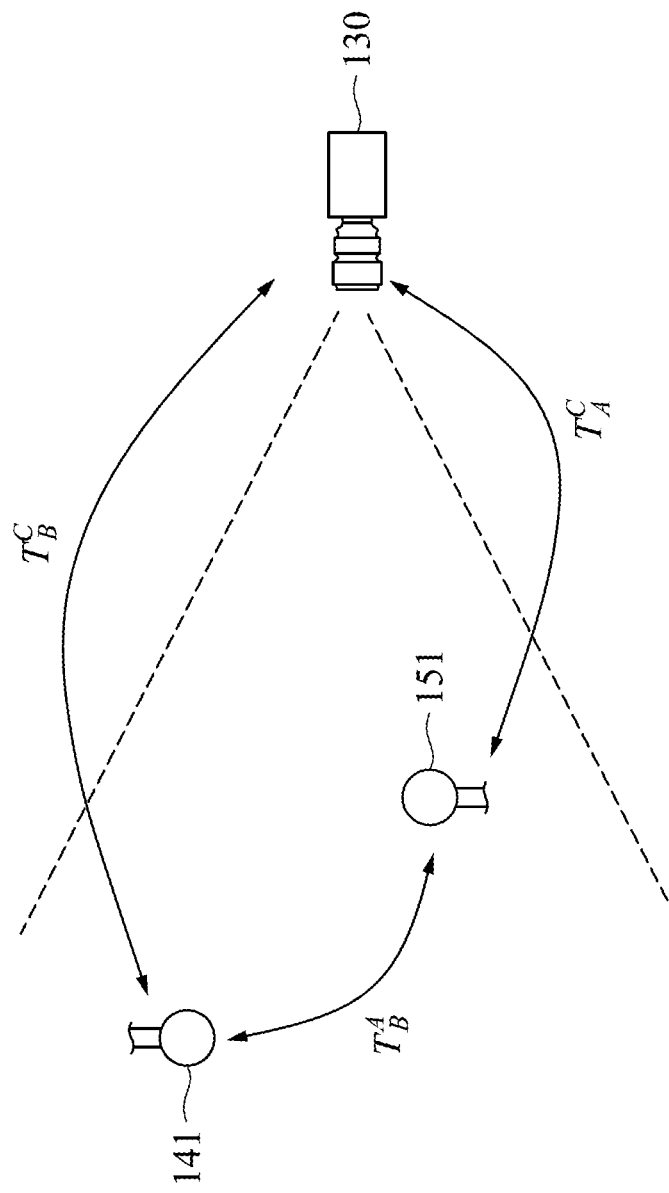
FIG. 3 illustrates a schematic diagram for illustrating steps of the operation image positioning method according to some embodiments of the present invention.

FIG. 3 illustrates a schematic diagram for illustrating steps S1-S4 of the operation image positioning method 1000 according to some embodiments of the present invention. As shown in FIGS. 1-3, in step S1, the point-cloud camera 130 captures the point-cloud image, and the point-cloud image contains the positioning mark 141 and the positioning mark 151.

Then, in step S2, the computer system 110 recognizes the positioning mark 151 within the point-cloud image so as to compute a first conversion module between the point-cloud camera 130 and the treated portion (i.e., the positioning mark 151). In some embodiments of the present invention, the first conversion module is, for example, a first matrix, and the first matrix can be expressed as $T_A^C$, in which 'C' corresponds to the point-cloud camera 130 and 'A' corresponds to the positioning mark 151 (i.e., the treated portion). In some embodiments of the present invention, the first matrix includes information such as displacement and rotation in the three-dimensional space so as to record the posture of the positioning mark 151. Specifically, in the above recognized process, the coordinates of the positioning mark 151 in the point-cloud image are converted into a conversion model in the three-dimensional point-cloud space, and this conversion can be performed according to the point-cloud data of the point-cloud camera 130. The conversion can also be obtained through appropriate computer vision technology, but the present invention does not limit how to calculate the conversion.

The details of step S1 and step S2 are described as follows. Firstly, the X-ray imaging machine 140 is used to capture the X-ray image, and the X-ray image contains the positioning mark 151, and at the same time, the point-cloud camera 130 captures the point-cloud image, and the point-cloud image contains the positioning mark 151. The computer system 110 can recognize the positioning mark 151 within the X-ray image and the point-cloud image through image processing method or computer vision method. For example, the positioning mark 151 has a specific pattern, so that the computer system 110 can recognize the positioning mark 151 within the X-ray image according to the preset pattern. For example, the positioning mark 151 has a specific structural feature, so that the computer system 110 can recognize the positioning mark 151 within the point-cloud image according to the preset structural feature. After the positioning mark 151 is recognized, a conversion module (i.e., a first conversion module) between the coordinate system of the X-ray imaging machine 140 and the coordinate system of the point-cloud camera 130 can be calculated. Specifically, the coordinates of the positioning mark 151 in the coordinate system of the X-ray imaging machine 140 are expressed as a vector A, and the coordinates of the positioning mark 151 in the coordinate system of the point-cloud camera 130 are expressed as a vector C. After pairing the vector A and the vector C, the aforementioned conversion model (i.e., the first conversion model) can be represented by the first matrix $T_A^C$ which is calculated according to the following formula $A=T_A^C C$.

Then, in step S3, the computer system 110 recognizes the positioning mark 141 within the point-cloud image so as to compute a second conversion module between the point-cloud camera 130 and the received part 143 of the X-ray imaging machine 140 (i.e., the positioning mark 141). In some embodiments of the present invention, the second conversion module is, for example, a second matrix, and the second matrix can be expressed as $T_B^C$, in which 'B' corresponds to the positioning mark 141 (i.e., the received part 143 of the X-ray imaging machine 140). In some embodiments of the present invention, the second matrix includes information such as displacement and rotation in the three-dimensional space so as to record the posture of the positioning mark 141. Specifically, in the above recognized process, the coordinates of the positioning mark 141 in the point-cloud image are converted into a conversion model in the three-dimensional point-cloud space, and this conversion can be performed according to the point-cloud data of the point-cloud camera 130. The conversion can also be obtained through appropriate computer vision technology, but the present invention does not limit how to calculate the conversion.

Then, in step S4, the computer system 110 computes a third conversion module between the treated portion (i.e., the positioning mark 151) and the received part 143 of the X-ray imaging machine 140 (i.e., the positioning mark 141) according to the first conversion module and the second conversion module.

In some embodiments of the present invention, the third conversion module is a third matrix, and the third matrix can be expressed as $T_B^A$, in which $T_B^C=T_A^C \times T_B^A$. In other words, the third matrix $T_B^A$ can be calculated according to the following formula $T_B^A=T_A^{C^{-1}} \times T_B^C$.

Figure 4:
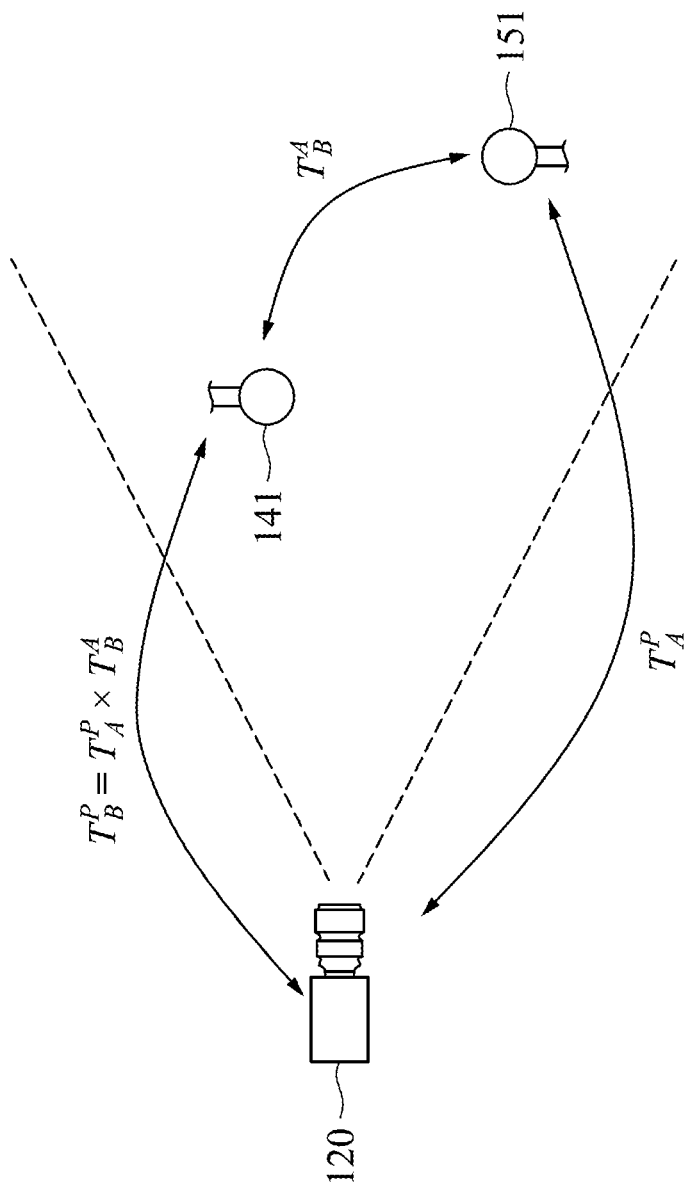
FIG. 4 illustrates a schematic diagram for illustrating steps of the operation image positioning method according to some embodiments of the present invention.

FIG. 4 illustrates a schematic diagram for illustrating steps S5-S7 of the operation image positioning method 1000 according to some embodiments of the present invention. As shown in FIG. 1, FIG. 2 and FIG. 4, in step S5, the image positioning camera 120 captures the positioning image, and the positioning image contains the positioning mark 151.

In step S6, the computer system 110 recognizes the positioning mark 151 within the positioning image so as to compute a fourth conversion module between the image positioning camera 120 and the treated portion (i.e., the positioning mark 151). In some embodiments of the present invention, the fourth conversion module is, for example, a fourth matrix, and the fourth matrix can be expressed as $T_A^P$, in which 'P' corresponds to the image positioning camera 120. In some embodiments of the present invention, the fourth matrix includes information such as displacement and rotation in the three-dimensional space so as to record the posture of the positioning mark 151. Specifically, in the above recognized process, the coordinates of the positioning mark 151 in the positioning image are converted into a conversion model in the three-dimensional space, and this conversion can be performed according to the image positioning information of the image positioning camera 120. The conversion can also be obtained through appropriate computer vision technology, but the present invention does not limit how to calculate the conversion.

The details of step S5 and step S6 are described as follows. Firstly, the X-ray imaging machine 140 is used to capture the X-ray image, and the X-ray image contains the positioning mark 151, and at the same time, the image positioning camera 120 captures the positioning image, and the positioning image contains the positioning mark 151. The computer system 110 can recognize the positioning mark 151 within the X-ray image and the positioning image through image processing method or computer vision method. For example, the positioning mark 151 has a specific pattern, so that the computer system 110 can recognize the positioning mark 151 within the X-ray image and the positioning image according to the preset pattern. After the positioning mark 151 is recognized, a conversion module (i.e., the fourth conversion module) between the coordinate system of the X-ray imaging machine 140 and the coordinate system of the image positioning camera 120 can be calculated. Specifically, the coordinates of the positioning mark 151 in the coordinate system of the X-ray imaging machine 140 are expressed as a vector A, and the coordinates of the positioning mark 151 in the coordinate system of the image positioning camera 120 are expressed as a vector P. After pairing the vector A and the vector P, the aforementioned conversion model (i.e., the fourth conversion model) can be represented by the fourth matrix $T_A^P$ which is calculated according to the following formula $A=T_A^P P$.

Then, in step S7, the computer system 110 computes a fifth conversion module between the image positioning camera 120 and the received part 143 of the X-ray imaging machine 140 (i.e., the positioning mark 141) according to the third conversion module and the fourth conversion module. In some embodiments of the present invention, the fifth conversion module is a fifth matrix, and the fifth matrix can be expressed as $T_B^P$, and the fifth matrix $T_B^P$ can be calculated according to the following formula $T_B^P=T_A^P \times T_B^A$.

As shown in FIG. 1 and FIG. 2, in step S8, the X-ray imaging machine 140 captures the X-ray image of the treated portion.

Then, in step S9, the computer system 110 combines the X-ray image captured by the X-ray imaging machine 140 and the positioning image captured by the image positioning camera 120 according to the fifth conversion module (i.e., the fifth matrix $T_B^P$), so as to provide a navigation interface. The computer system 110 can provide a navigation interface according to the fifth conversion module $T_B^P$. For example, the computer system 110 can further calculate the position of the image positioning camera 120 relative to the positioning mark 151, thereby displaying a virtual object at the corresponding position in the navigation interface to represent the corresponding spine bone (i.e., the positioning mark 151). Specifically, the fifth conversion module (i.e., the fifth matrix $T_B^P$) represents the conversion module between the coordinate system of the X-ray imaging machine 140 and the coordinate system of the image positioning camera 120. Therefore, as long as the image positioning camera 120 is continuously used to track the position of the positioning mark 151 in the coordinate system of the image positioning camera 120, after conversion through the fifth conversion module, the real-time position information of the positioning mark 151 in the coordinate system of the X-ray imaging machine 140 can be obtained in real time on the X-ray image. During the operation, if the positioning mark 151 moves, the computer system 110 can change the position of the virtual object in the navigation interface, so that the corresponding positioning of the positioning mark 151 in the navigation interface can still be known without using the X-ray imaging machine 140 to repeatedly capture X-ray images, thereby preventing the repeatedly photography of the X-ray imaging machine 140 from injuring the human body.

In some embodiments of the present invention, the navigation interface can be displayed on the screen of the computer system 110, but in some other embodiments, the navigation interface can also be displayed on the head-mounted device of the computer system 110, the tablet computer of the computer system 110, or the transparent display of the computer system 110, but the present invention is not limited thereto. In some embodiments of the present invention, any virtual reality (VR) technology, augmented reality (AR) technology, alternative reality technology or mixed reality technology can be used to form the navigation interface, but the present invention is not limited thereto. For example, the image processing technology can be used to segment the positioning mark 151 in the X-ray image to generate corresponding virtual objects, and thus the doctor can know the current position of the spine bone (i.e., the positioning mark 151) through the navigation interface.

It is noted that each step in FIG. 2 can be implemented as plural program codes or circuits, but the present invention is not limited thereto. In addition, the method in FIG. 2 can be used in combination with the above embodiments, or can be used alone. In other words, other steps may also be added between the steps in FIG. 2.

Specifically, the present invention realizes dual positioning correction through the point-cloud camera and the image positioning camera. When capturing the X-ray image, in addition to using the positioning image captured by the image positioning camera to detect the relative relationship between the X-ray imaging machine and the positioning mark, the present invention further uses point cloud scanning technology to accurately calculate the relative relationship between the X-ray imaging machine and the positioning mark and correct the relative relationship based on the point-cloud information. In this way, the error value of the capturing position recorded by the X-ray imaging machine can be greatly reduced. In other words, the present invention uses point cloud information to correct the spatial relationship between the positioning mark on the treated portion and the positioning mark on the X-ray imaging machine, thereby reducing the error in positioning longitude caused by the image positioning camera.

For the calculation of the projection position in the X-ray image of the X-ray imaging machine (i.e., the C-arm X-ray equipment), the conventional surgical navigation system only calculates the position information of the positioning mark on the X-ray imaging machine and the position information of the positioning mark on the treated portion through the image positioning camera. Therefore, its positioning accuracy will be affected by the positioning accuracy of the image positioning camera, and its spatial positioning root mean square error (RMSE) is about 0.5 mm. Therefore, the maximum error in the spatial relationship between the positioning mark on the X-ray imaging machine and the positioning mark on the treated portion may reach 1 mm. When capturing image based on the X-ray imaging machine (i.e., the C-arm X-ray equipment), compared with surgical actions, the X-ray imaging machine (i.e., the C-arm X-ray equipment) and the treated portion are relatively static (i.e., there is no need for real-time positioning). Therefore, the present invention further introduces the point cloud scanning technology to correct the error generated by the positioning accuracy of the image positioning camera, thereby improving the accuracy of the surgical navigation system. Specifically, the present invention eliminates main image errors, so that the real-time spatial positioning error has a greater tolerance.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An operation image positioning method, executed by a computer system, comprising:
   capturing a point-cloud image by a point-cloud camera, wherein the point-cloud image contains a first positioning mark and a second positioning mark, wherein the first positioning mark is fixed on a treated portion and the second positioning mark is fixed on an X-ray imaging machine;
   recognizing the first positioning mark within the point-cloud image by the computer system so as to compute a first conversion module between the point-cloud camera and the treated portion;
   recognizing the second positioning mark within the point-cloud image by the computer system so as to compute a second conversion module between the point-cloud camera and the X-ray imaging machine;
   computing a third conversion module between the treated portion and the X-ray imaging machine, by the computer system, according to the first conversion module and the second conversion module;
   capturing a positioning image by an image positioning camera, wherein the positioning image contains the first positioning mark;
   recognizing the first positioning mark within the positioning image by the computer system so as to compute a fourth conversion module between the image positioning camera and the treated portion; and
   computing a fifth conversion module between the image positioning camera and the X-ray imaging machine, by the computer system, according to the third conversion module and the fourth conversion module.

2. The operation image positioning method of claim 1, further comprising:
   capturing an X-ray image of the treated portion by the X-ray imaging machine; and
   combining the X-ray image and the positioning image according to the fifth conversion module, by the computer system, so as to provide a navigation interface.

3. The operation image positioning method of claim 1, wherein the X-ray imaging machine is a C-arm X-ray equipment having a transmitted part and a received part, wherein the second positioning mark is fixed on the received part.

4. The operation image positioning method of claim 1, wherein each of the first positioning mark and the second positioning mark has a structural feature recognized by the point-cloud camera, wherein the structural feature of the first positioning mark is different from the structural feature of the second positioning mark.

5. The operation image positioning method of claim 1, wherein each of the first positioning mark and the second positioning mark has a pattern recognized by the image positioning camera, wherein the pattern of the first positioning mark is different from the pattern of the second positioning mark.

6. The operation image positioning method of claim 1, wherein the first conversion module is a first matrix $T_A^C$, wherein the second conversion module is a second matrix $T_B^C$, wherein the third conversion module is a third matrix $T_B^A$, wherein $T_B^C = T_A^C \times T_B^A$.

7. The operation image positioning method of claim 6, wherein the fourth conversion module is a fourth matrix $T_A^P$, wherein the fifth conversion module is a fifth matrix $T_B^P$, wherein $T_B^P = T_A^P \times T_B^A$.

8. An operation image positioning system, comprising:
a first positioning mark fixed on a treated portion;
a second positioning mark fixed on an X-ray imaging machine;
a point-cloud camera operable to capture a point-cloud image, wherein the point-cloud image contains the first positioning mark and the second positioning mark;
an image positioning camera operable to capture a positioning image, wherein the positioning image contains the first positioning mark; and
a computer system communicatively connected to the point-cloud camera and the image positioning camera so as to receive the point-cloud image and the positioning image, wherein the computer system performs steps of:
recognizing the first positioning mark within the point-cloud image so as to compute a first conversion module between the point-cloud camera and the treated portion;
recognizing the second positioning mark within the point-cloud image so as to compute a second conversion module between the point-cloud camera and the X-ray imaging machine;
computing a third conversion module between the treated portion and the X-ray imaging machine according to the first conversion module and the second conversion module;
recognizing the first positioning mark within the positioning image so as to compute a fourth conversion module between the image positioning camera and the treated portion; and
computing a fifth conversion module between the image positioning camera and the X-ray imaging machine according to the third conversion module and the fourth conversion module.

9. The operation image positioning system of claim 8, wherein the X-ray imaging machine is operable to capture an X-ray image of the treated portion, wherein the computer system is communicatively connected to the X-ray imaging machine, wherein the computer system further performs steps of:
combining the X-ray image and the positioning image according to the fifth conversion module so as to provide a navigation interface.

10. The operation image positioning system of claim 8, wherein the X-ray imaging machine is a C-arm X-ray equipment having a transmitted part and a received part, wherein the second positioning mark is fixed on the received part.

11. The operation image positioning system of claim 8, wherein each of the first positioning mark and the second positioning mark has a structural feature recognized by the point-cloud camera, wherein the structural feature of the first positioning mark is different from the structural feature of the second positioning mark.

12. The operation image positioning system of claim 8, wherein each of the first positioning mark and the second positioning mark has a pattern recognized by the image positioning camera, wherein the pattern of the first positioning mark is different from the pattern of the second positioning mark.

13. The operation image positioning system of claim 8, wherein the first conversion module is a first matrix $T_A^C$, wherein the second conversion module is a second matrix $T_B^C$, wherein the third conversion module is a third matrix $T_B^A$, wherein $T_B^C = T_A^C \times T_B^A$.

14. The operation image positioning system of claim 13, wherein the fourth conversion module is a fourth matrix $T_A^P$, wherein the fifth conversion module is a fifth matrix $T_B^P$, wherein $T_B^P = T_A^P \times T_B^A$.

15. The operation image positioning system of claim 8, wherein the point-cloud camera is a depth camera or a LiDAR scanner, wherein the image positioning camera is a visible light camera.

* * * * *